US007541331B2

(12) United States Patent
Killian et al.

(10) Patent No.: US 7,541,331 B2
(45) Date of Patent: Jun. 2, 2009

(54) SURFACTANT TREATMENT REGIMEN

(75) Inventors: Anthony Killian, Easton, PA (US); Christopher Schaber, Columbus, NJ (US); Robert Segal, Gwynedd Valley, PA (US); Carlos Guardia, Philadelphia, PA (US)

(73) Assignee: Discovery Laboratories, Inc., Warrington, PA (US)

( * ) Notice: Subject to any disclaimer, the term of this patent is extended or adjusted under 35 U.S.C. 154(b) by 0 days.

(21) Appl. No.: 11/326,885

(22) Filed: Jan. 6, 2006

(65) Prior Publication Data

US 2006/0194728 A1 Aug. 31, 2006

Related U.S. Application Data

(60) Provisional application No. 60/641,805, filed on Jan. 6, 2005.

(51) Int. Cl.
*A01N 37/18* (2006.01)
*A61K 38/00* (2006.01)
*A01N 33/00* (2006.01)

(52) U.S. Cl. .............................. 514/2; 514/12; 514/13; 514/579

(58) Field of Classification Search .................. None
See application file for complete search history.

(56) References Cited

U.S. PATENT DOCUMENTS

| | | | |
|---|---|---|---|
| 4,861,756 A | 8/1989 | Jackson | 514/11 |
| 4,918,161 A | 4/1990 | Steinbrink | 530/300 |
| 5,006,343 A | 4/1991 | Benson et al. | 424/450 |
| 5,024,995 A | 6/1991 | Robertson et al. | 514/21 |
| 5,164,369 A | 11/1992 | Cochrane et al. | 514/12 |
| 5,223,481 A | 6/1993 | Curstedt et al. | 514/12 |
| 5,238,920 A | 8/1993 | Sarin et al. | 514/12 |
| 5,260,273 A | 11/1993 | Cochrane et al. | 514/12 |
| 5,272,252 A | 12/1993 | McLean et al. | 530/327 |
| 5,302,481 A | 4/1994 | Ong | 430/108.24 |
| 5,407,914 A | 4/1995 | Cochrane et al. | 514/12 |
| 5,455,227 A | 10/1995 | Curstedt et al. | 514/14 |
| 5,753,621 A | 5/1998 | Dhaon et al. | 514/12 |
| 5,789,381 A | 8/1998 | Cochrane et al. | 514/13 |
| 5,827,825 A | 10/1998 | Takei et al. | 514/12 |
| 5,840,527 A | 11/1998 | Schilling, Jr. et al. | 435/69.1 |
| 5,863,563 A * | 1/1999 | Scheele | 424/717 |
| 5,874,406 A | 2/1999 | Schafer et al. | 514/12 |
| 5,891,844 A | 4/1999 | Hafner | 514/7 |
| 6,013,619 A | 1/2000 | Cochrane et al. | 514/12 |
| 6,022,955 A | 2/2000 | Sarin et al. | 530/410 |
| 6,613,734 B2 | 9/2003 | Cochrane et al. | 514/2 |
| 6,660,833 B1 | 12/2003 | Walther et al. | 530/324 |
| 2006/0078506 A1 | 4/2006 | Niven et al. | 424/45 |

FOREIGN PATENT DOCUMENTS

| | | |
|---|---|---|
| WO | 86/03408 A1 | 6/1986 |
| WO | 89/04326 A1 | 5/1989 |
| WO | 97/19701 A2 | 6/1997 |
| WO | 2002/062289 A2 | 8/2002 |
| WO | 2005/115520 A1 | 12/2005 |
| WO | 2006/026237 A1 | 3/2006 |

OTHER PUBLICATIONS

Hudak et al., A multicenter randomized masked comparison trial of synthetic surfactant versus calf lung surfactant extract in the prevention of neonatal respiratory distress syndrome, Pediatrics, 1997, 100(1): 39-50.*
Cochrane et al., The efficiency and safety of KL4-surfactant in preterm infants with respiratory distress syndrome, Am. J. Respir. Crit. Care Med.,1996, 153(1): 404-410.*
Ngo et al., in The Protein Folding Problem and Tertiary Structure Prediction, 1994, Merz et al. (ed.), Birkhauser, Boston, MA, pp. 433 and 492-495.*
Spear, M. Bronchopulmonary Dysplasia, Retrieved from the Internet <URL: www.kidshealth.org/parent/medical/lungs/bpd.html>.*
Cochrane et al., Pulmonary surfactant protein B (SP-B): structure-function relationships, 1991, Science, vol. 254: 566-568.*
Bancalari, E. et al., "Bronchopulmonary Dysplasia: Changes in Pathogenesis, Epidemiology and Definition," *Semin. Neonatol.*, vol. 8, pp. 63-71, 2003.
Cochrane, C.G. et al., "The Efficacy and Safety of $KL_4$-Surfactant in Preterm Infants with Respiratory Distress Syndrome," Am. J. Respir. Crit. Care Med., vol. 153(1), pp. 404-410, 1996.
Enhorning, G., "Pulsating Bubble Technique for Evaluating Pulmonary Surfactant," *J. Appl. Physiol.*, vol. 43, pp. 198-203, 1977.
Glasser, S.W. et al., "cDNA and Deduced Amino Acid Sequence of Human Pulmonary Surfactant-Associated Proteolipid SPL(Phe)," *Proc. Natl. Acad. Sci.*, vol. 84(12), pp. 4007-4011, 1987.
Gortner, L. et al., "Early Treatment of Respiratory Distress Syndrome with Bovine Surfactant in Very Preterm Infants: A Multicenter Controlled Clinical Trial," *Pediatric Pulmonology*, vol. 14(1), pp. 4-9, 1992.
Hopp, T.P. and Woods, K.R., "Prediction of Protein antigenic Determinants from Amino Acid Sequences," *Proc. Natl. Acad. Sci. USA*, vol. 78(6), pp. 2824-3828, 1981.
Hudak, M.L. et al., "A Multicenter Randomized Masked Comparison Trial of Synthetic Surfactant Versus Calf Lung Surfactant Extract in the Prevention of Neonatal Respiratory Distress Syndrome," *Pediatrics*, vol. 100(1), pp. 39-50, 1997.
Jobe, A.H. and Bancalari, E., "Bronchopulmonary Dysplasia," *Am. J. Respir. Crit. Care Med.*, vol. 163, pp. 1723-1729, 2001.
King, R.J. and Clements, J.A., "Surface Active Materials from Dog Lung. II. Composition and Physiological Correlations," *Am. J. Physiol.*, vol. 223, pp. 715-726, 1972.
Merrifield, R.B., "Solid Phase Peptide Synthesis. I. The Synthesis of a Tetrapeptide," J. Am. Chem.. Soc., vol. 85, pp. 2149-2154, 1962.
Morley, C. and Davis, P., "Surfactant Treatment for Premature Lung Disorders: A Review of Best Practices in 2002," *Ped. Resp. Rev.*, vol. 5(Suppl. A), pp. S299-S304, 2004.

(Continued)

Primary Examiner—Delia M Ramirez
Assistant Examiner—Jae W Lee
(74) Attorney, Agent, or Firm—Potter Anderson & Corroon LLP

(57) ABSTRACT

Regimens for the therapeutic or prophylactic administration of pulmonary surfactant to infants exhibiting or at risk of developing bronchopulmonary dysplasia are disclosed.

45 Claims, No Drawings

OTHER PUBLICATIONS

Ngo, J.T. et al., Computational Complexity, Protein Structure Prediction, and the Levinthal Paradox, *in The Protein Folding Problem and Teritiary Structure Prediction*, 1994, Merz et al. (ed)., Birkhauser, Boston, MA, pp. 433 and 492-495.

Revak, S.D. et al., "Efficacy of Synthetic Peptide-Containing Surfactant in the Treatment of Respiratory Distress Syndrome in Preterm Infant Rhesus Monkeys," *Am. Rev. Respir. Dis.*, vol. 134, pp. 1258-1265, 1986.

Revak, S.D. et al., "Reconstitution of Surfactant Activity Using Purified Human Apoprotein and Phospholipids Measured In Vitro and In Vivo," *Am. Rev. Respir. Dis.*, vol. 134(6), pp. 1258-1265, 1986.

Robertson, B., "Surfactant Substitution; Experimental Models and Clinical Applications," *Lung*, vol. 158, pp. 57-68, 1980.

Stewart, J.M. and Young, J.D., "Laboratory Techniques in Solid Phase Peptide Synthesis," *Solid Phase Peptides Synthesis*, Chap. 2, W.H. Freeman & Co., pp. 27-62, 1969.

Zalipsky, S., "Chemistry of Polyethylene Glycol Conjugates with Biologically Active Molecules," *Adv. Drug. Del. Rev.*, vol. 16, pp. 157-182, 1995.

Zhao, X. and Harris, J.M., "Novel Degradable Poly(ethylene glycol) Esters for Drug Delivery," *A.C.S. Symposium Series*, vol. 680, pp. 458-472, 1997.

Ballard, P., et al., "Surfactant Protein Profile of Pulmonary Surfactant in Premature Infants", *American Journal Of Respiratory And Critical Care Medicine*, vol. 168, pp. 1124-1128, 2003.

Bissinger, R. et al., "Secondary Surfactant Deficiency in Neonates", *Journal of Perinatology.*, vol. 24, pp. 663-666, 2004.

Cochrane, C., et al., "The Efficacy and Safety of $KL_4$-Surfactant in Preterm Infants with Respiratory Distress Syndrome", *American Journal Of Respiratory And Critical Care Medicine*, vol. 153, pp. 404-410, 1996.

Cogo, P., et al., "Surfactant Kinetics in Preterm Infants on Mechanical Ventilation Who Did Not Develop Bronchopulmonary Dysplasia", *Pediatric Critical Care*, vol. 31, No. 5, pp. 1532-1538, 2003.

Davis, J., et al., "High-Frequency Jet Ventilation and Surfactant Treatment of Newborns With Severe Respiratory Failure", *Pediactric Pulmonology*, vol. 13, pp. 108-112, 1992.

Hoekstra, R., et al., "Improved Neonatal Survival Following Multiple Doses of Bovine Surfactant in Very Premature Neonates at Risk for Respiratory Distress Syndrome", *Pediatrics*, vol. 88, No. 1, pp. 10-18, 1991.

McMillan, D., et al., "Effects of Two Rescue Doses of Synthetic Surfactant in 344 Infants with Respiratory Distress Syndrome Weighing 750 to 1249 Grams: A Double-blind, Placebo-Controlled Multicenter", *The Journal of Pediatrics*, vol. 126, No. 5, Part 2, pp. 90-102, 1995.

Merrill, J., et al., "Dysfunction of Pulmonary Surfactant in Chronically Ventilated Premature Infants", *Pediactric Research*, vol. 56, No. 6, pp. 108-112, 1992.

Pandit, P., et al., "Surfactant Replacement in Neonates With Early Chronic Lung Disease", *Pediatrics*, vol. 95, pp. 851-854, 1995.

Smyth, J., et al., "Double-blind, Randomized, Placebo-Controlled Canadian Multicenter Trial of Two Doses of Synthetic Surfactant or Air Placebo in 224 Infants Weighting 500 to 749 Grams with Respiratory Distress Syndrome", *The Journal of Pediatrics*, vol. 126, No. 5, Part 2, pp. S81-S89, 1995.

Soll, R., et al., "Multicenter Trial of Single-Dose Modified Bovine Surfactant Extract (Survanta) for Prevention of Respiratory Distress Syndrome", Pediatrics, vol. 85, No. 6, 1990.

* cited by examiner

SURFACTANT TREATMENT REGIMEN

CROSS-REFERENCE TO RELATED APPLICATIONS

This application claims benefit under 35 U.S.C. §119(e) to application Ser. No. 60/641,805 filed Jan. 6, 2005, the disclosure of which is incorporated by reference in its entirety.

FIELD

This invention relates to the treatment of pulmonary disorders. In particular, regimens for the treatment or prevention of bronchopulmonary dysplasia and related disorders are provided, featuring the use of pulmonary surfactants.

BACKGROUND

Various patents, patent publications and scientific articles may be referred to throughout the specification. The contents of each of these documents are incorporated by reference herein, in their entireties.

Natural pulmonary surfactants (PS) are protein/lipid compositions that are produced naturally in the lungs and are critical to the lungs' ability to absorb oxygen. They cover the entire alveolar surface of the lungs and the terminal conducting airways leading to the alveoli. Surfactants facilitate respiration by continually modifying the surface tension of the fluid normally present within the alveoli. In the absence of sufficient surfactant, or should the surfactant degrade, the alveoli tend to collapse and the lungs do not absorb sufficient oxygen. By lowering the surface tension of the terminal conducting airways, surfactant maintains patency, i.e., keeps airways open. Loss of patency leads to loss of patency obstruction of the airway and compromised pulmonary function. Human surfactants primarily contain: phospholipids, the major one being dipalmitoyl phosphatidyl-choline (DPPC), and four surfactant polypeptides, A, B, C and D with surfactant protein B (SP-B) being the most essential for respiratory function. Natural and synthetic pulmonary surfactants are commonly used to treat respiratory distress syndrome in premature infants shortly after birth.

Bronchopulmonary dysplasia (BPD or BD), also referred to as chronic lung disease (CLD), is a common, occasionally life threatening, lung disease typically occurring in premature infants who survive respiratory distress syndrome (RDS) and other complications of prematurity. With the near universal adoption of antenatal steroids and post-natal use of exogenous lung surfactants, large numbers of at-risk low birth weight infants now survive the acute lung disease of prematurity only to develop chronic lung disease. Prior to the widespread use of synthetic or animal derived surfactants, BPD was histologically characterized by airway injury and fibrosis. Since the advent of surfactant replacement therapy, infants appear to experience less airway and fibrotic involvement than described in earlier reports but have abnormalities in alveolarization and vascularization. The change in the nature of the condition has led neonatologists to refer to a "new BPD". BPD can also develop in term infants who require respiratory support at birth or soon thereafter.

Surfactant therapy has decreased the frequency with which larger, moderately premature infants develop the disease, but the survival benefits of surfactant in extremely premature infants has resulted in a shift in the incidence of BPD toward smaller, more premature babies. Post-natal steroids in antiinflammatory doses are known to modestly decrease the physiologic consequences of BPD, but at the expense of neuro-developmental outcomes. Further, steroids may decrease alveolarization. Vitamin A derivatives stimulate alveolarization in animals, but clinical results have been modest. Despite an intriguing rationale, antioxidants have proven to be of little value. Whether inhaled nitric oxide will decrease the likelihood of BPD in very low birth weight infants awaits the outcome of ongoing clinical trials.

Causes of BPD or CLD are probably multi-factorial. However, the pathophysiologic antecedents and consequences of BPD may suggest a new approach to prevention with drugs already in clinical use. Decreased lung compliance as a consequence of initially mild pulmonary edema has been shown to correlate with subsequent development of BPD. Neutrophil migration to the lung increases in the presence of pulmonary edema and hyperoxia. When these cells are activated, they release proteases and inflammatory mediators including oxidants that can further injure the lung. These events degrade pulmonary function necessitating mechanical ventilation for many infants initially weaned from the ventilator and increasing ventilator requirements for those never able to wean. Surfactant is itself a target of proteases, oxidant species and small molecule mediators and can be inactivated by many plasma proteins found in bronchoalveolar fluid in the presence of capillary leak.

Treatments to prevent or ameliorate BPD and related pulmonary disorders are needed. The present invention is directed to this and other important needs.

BRIEF SUMMARY

One aspect of the invention features a method for treating or preventing BPD in an infant treated with pulmonary surfactant for respiratory distress syndrome ("RDS"). Following the treatment for respiratory distress syndrome with pulmonary surfactant, pulmonary surfactant is administered to the infant in an amount and for a time effective to treat or prevent the BPD. Typically, administration of the pulmonary surfactant for BPD is initiated after the treatment of the respiratory distress syndrome with pulmonary surfactant, for instance, at the next dosage interval following completion of the treatment for RDS, at day 3 of life of the infant, or whenever the treatment for RDS is completed. In certain embodiments, administration of the pulmonary surfactant is continued through at least 36 weeks post-menstrual age ("PMA") of the infant or alternatively through at least 28 days post-natal age of the infant. In certain embodiments, administration of the pulmonary surfactant is continued through at least day 14 or day 18 of life of the infant. In certain embodiments, treatment is initiated anytime from day 3 of life of the infant to day 10 or even later, e.g., day 14 or 18 of life of the infant or later.

Another aspect of the invention features a method for treating or preventing BPD in an infant requiring respiratory support. The pulmonary surfactant is administered to the infant in an amount and for a time effective to treat or prevent the BPD. In certain embodiments, the PS is administered until the infant no longer requires respiratory support. In certain embodiments, the PS is administered at or after day 1 of life of the infant and is continued through at least 36 weeks PMA or alternatively through at least 28 days post-natal age of the infant. In certain embodiments, the administering is initiated at day 1 of life of the infant or at day 3 of life of the infant. In certain embodiments, the administering is initiated before the infant has been diagnosed with BPD and the infant is treated with pulmonary surfactant at least once after day 2, 3, 4, 5, 6, 7, 8, 9, or 10 of life of the infant. In certain embodiments, the administering is initiated at day 1 of life of the infant or at day 2, of life of the infant and the infant is treated with pulmonary surfactant at least once after day 2, 3, 4, 5, 6, 7, 8, 9, or 10 of life of the infant. In some of these embodiments, treatment is continued through at least day 10, day 14, or day 18 of life of the infant. In some of these embodiments, administration of PS is initiated anytime from day 3 to day 18, day 3 to day 14, or day 3 to day 10 of life of the infant. The infant requiring respiratory support may or may not exhibit respiratory distress syndrome.

Methods of administering pulmonary surfactant to an infant are known in the art. In certain embodiments, administration is by endotracheal administration. In other embodiments, administration is by aerosolization and inhalation. The term "inhalation" includes, for example, both inhalation of a dry powder and inhalation of a wet aerosol.

In certain embodiments, the aforementioned treatment protocol is accompanied by another respiratory therapy, such as mechanical ventilation, continuous positive airway pressure (CPAP) including nasal CPAP (nCPAP) or administration of other therapeutic agents.

In a preferred embodiment, the method comprises administering a synthetic pulmonary surfactant. Particularly preferred is a pulmonary surfactant that contains a peptide having a sequence of SEQ ID NO:1.

Other features and advantages of the invention will be understood from the detailed description and examples that follow.

DETAILED DESCRIPTION

Unless otherwise specified, all medical procedures described or referred to herein are performed in accordance with current standards of care understood by physicians and/or other healthcare practitioners.

It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a peptide" includes a combination of two or more peptides, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Polypeptide," "peptide" "peptoids" and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid mimetics refers to chemical compounds that have a structure that is different from the general chemical structure of an amino acid, but that functions in a manner similar to a naturally occurring amino acid. Non-natural residues are well described in the scientific and patent literature; a few exemplary non-natural compositions useful as mimetics of natural amino acid residues and guidelines are described below. Mimetics of aromatic amino acids can be generated, for example, by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

"Peptide" includes peptides which are conservative variations of those peptides specifically exemplified herein. "Conservative variation" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. "Conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. "Cationic" as used herein refers to any peptide that possesses a net positive charge at pH 7.4. The biological activity of the peptides can be determined by standard methods known to those of skill in the art and described herein.

Peptides of the invention can be synthesized by methods known in the art. For example, in certain embodiments, commonly used methods such as t-BOC or FMOC protection of alpha-amino groups can be used. Both methods involve stepwise syntheses whereby a single amino acid is added at each step starting from the C terminus of the peptide (See, Coligan et al., *Current Protocols in Immunology*, Wiley Interscience, 1991, Unit 9). Peptides of the invention can be synthesized, for example, by the well known solid phase peptide synthesis methods described in Merrifield, *J. Am. Chem. Soc.* 85: 2149, 1962, and Stewart and Young, 1969, *Solid Phase Peptides Synthesis*, pp. 27-62, using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

"Recombinant" when used with reference to a protein indicates that the protein has been modified by the introduction of a heterologous nucleic acid or protein or the alteration of a native nucleic acid or protein.

For the purposes of present invention, BPD is diagnosed at 28 days of age or thereabout, 36 weeks PMA or thereabout, or as set forth in Table 1 below. An infant that either remains on mechanical ventilation or requires supplemental oxygen in order to maintain oxygen saturation levels ("SaO$_2$") greater than or equal to 90% (with the exception of infants requiring supplemental oxygen during feedings) at 36 weeks PMA or at 28 days of age is said to have BPD. Generally, chest x-rays will also be performed for infants at 28 days of age in order to confirm the BPD diagnosis. The x-ray of lungs with BPD often have a bubbly, sponge-like appearance. X-rays are diagnostic tests which use invisible electromagnetic energy beams to produce images of internal tissues, bones, and organs onto film.

Alternatively, BPD can be diagnosed using the criteria set forth in Table 1 below from Jobe and Bancalari, *Am J Respir Crit Care Med,* 2001, 163:1723-1729, incorporated herein by reference in its entirety for all purposes.

TABLE 1

| | Gestational Age | |
|---|---|---|
| | <32 weeks | ≧32 weeks |
| Time point of assessment | 36 weeks PMA or discharge to home, whichever comes first | >28 days but <56 days post-natal age or discharge to home, whichever comes first |
| | Infants have already been treated with oxygen >21% for at least 28 days plus | Infants have already been treated with oxygen >21% for at least 28 days plus |
| Mild BPD | Breathing room air at 36 weeks PMA or discharge, whichever comes first | Breathing room air by 56 days post-natal age or discharge, whichever comes first |
| Moderate BPD | Need for <30% oxygen at 36 weeks PMA or discharge, whichever comes first | Need for <30% oxygen at 56 days post-natal age or discharge, whichever comes first |
| Severe BPD | Need for ≧30% oxygen and/or positive pressure (e.g., PPV or NCPAPA) at 36 weeks PMA or discharge, whichever comes first | Need for ≧30% oxygen and/or positive pressure (e.g., PPV or NCPAPA) at 56 days post-natal age or discharge, whichever comes first |

Infants treated with oxygen >21% and/or positive pressure for nonrespiratory disease (e.g., central apnea or diaphragmatic paralysis) as provided in Table 1 do not have BPD unless they also develop parenchymal lung disease and exhibit clinical features of respiratory distress. A day of treatment with oxygen >21% means that the infant received oxygen >21 % for more than 12 hours on that day. Treatment with oxygen >21% and/or positive pressure at 36 weeks PMA, or at 56 days post-natal age or discharge, should not reflect an "acute" event, but should rather reflect the infant's usual daily therapy for several days preceding and following 36 weeks PMA, 56 days post-natal age, or discharge.

For the purposes of present invention, "Respiratory Distress Syndrome" is defined at being present in an infant at 24 hours of age with a need for a fraction of inspired oxygen ("FiO$_2$")≧0.30 combined with the demonstration of a reticulogranular pattern on a chest radiograph obtained between 20 and 28 hours of age.

"Supplemental oxygen" refers to any requirement for additional oxygen to maintain oxygen saturation levels >90%. This can include mechanical ventilation and/or CPAP if supplemental oxygen (≧21% FiO$_2$) is being given.

"Infant" includes neonatal infants. Typically a neonatal infant is an infant born prematurely or otherwise, under 4 weeks old. For the purposes used herein, infants are under 2 years old.

"Respiratory support" includes any intervention that treats respiratory illness including, for example, the administration of supplemental oxygen, mechanical ventilation, CPAP, albuterol treatment, and the like.

"Treating" refers to any indicia of success in the treatment or amelioration of the disease or condition, e.g., BPD. Treatment at Day 1 (or DOL 1) is the day on which Time 0 (time of birth) occurs and DOL 2, 3, and so on, begin at 00:00 (midnight) each subsequent day following Time 0.

"Preventing" refers to the prevention of the disease or condition, e.g., BPD, in the patient. For example, if an infant exhibiting respiratory distress syndrome, or requiring any form of respiratory support at birth, is treated with the methods of the present invention and is not later diagnosed with BPD, e.g., at 28 days of age or at 36 weeks PMA, it will be understood that BPD has been prevented in that infant.

"Surfactant activity" refers to the ability of any substance, such as an organic molecule, protein or polypeptide, either alone or in combination with other molecules, to lower surface tension at an air/water interface. The measurement can be made with a Wilhelmy Balance or pulsating bubble surfactometer by an in vitro assay. See, for example King et al, *Am. J. Physiol.* 1972, 223:715-726, or *Enhorning, J. Appl. Physiol.*, 1977, 43:198-203, each of which is incorporated herein by reference in its entirety. Briefly, the Enhorning Surfactometer (Surfactometer International, Toronto, Ontario) measures the pressure gradient (δP) across a liquid-air interface of a bubble that pulsates at a rate of 20 cycles/min between a maximal (0.55 mm) and minimal (0.4 mm) radius. The bubble, formed in a 37° C., water-enclosed, 20-μl sample chamber, is monitored through a microscopic optic while the pressure changes are recorded on a strip chart recorder calibrated for 0 and −2 cm H$_2$O. In addition, in vivo measurements of increases of compliance or airflow at a given pressure of air entering the lung can be readily made, such as in the assay of Robertson, *Lung,* 1980, 158:57-68, incorporated herein by reference in its entirety. In this assay, the sample to be assessed is administered through an endotracheal tube to fetal rabbits or lambs delivered prematurely by Caesarian section. (These "preemies" lack their own PS, and are supported on a ventilator.) Measurements of lung compliance, blood gases and ventilator pressure provide indices of activity. In vitro assays of surfactant activity, which is assessed as the ability to lower the surface tension of a pulsating bubble, and in vivo assays utilizing fetal rabbits is described in detail by Revak et al, *Am. Rev. Respir. Dis.,* 1986, 134:1258-1265.

In one aspect, the invention contemplates the therapeutic or prophylactic administration of pulmonary surfactant (PS) to infants exhibiting or at risk of developing bronchopulmonary dysplasia (BD or BPD). In one embodiment, PS administration is initiated in an infant exhibiting respiratory distress syndrome, following treatment of such syndrome with pulmonary surfactant or by another means (e.g., ventilation) or a combination thereof. Typically, infant RDS is treated via PS therapy within the first few hours to one or two days after birth. In the methods of the invention, administration of PS for the treatment or prevention of BPD is initiated following the RDS treatment, e.g., at day 2, 3, 4, 5, 6, 7, 8, 9, 10, 11, 12, 13, or 14 of life or thereabout, or whenever the treatment for RDS is completed. In certain embodiments, the infant will be treated with pulmonary surfactant at the next dosage interval appropriate for such treatment after completion of RDS treatment. For example, in some embodiments, where PS is administered as a liquid by intratracheal instillation, treatment with PS for BPD will be about 6 hours following the last treatment of PS for RDS. A clinician will be able to determine, based on administration protocols known in the art, when dosage of PS for the treatment of BPD should be initiated.

In certain embodiments, the infant may not receive PS therapy for RDS, but nonetheless can be administered PS to treat or prevent BPD, in accordance with the present invention. In certain embodiments, the treatment with PS will be initiated following the episode of respiratory distress syndrome. In certain preferred embodiments, the administering is initiated before the infant has been diagnosed with BPD and the infant is treated with pulmonary surfactant at least once after day 2, 3, 4, 5, 6, 7, 8, 9, or 10 of life of the infant. The administration of PS can be initiated, for example, at or after day 1, 2, 3, 4, 5, 6, 7, 8, 9, 10, 12, 13, 14 of life or therabout of the infant. Methods of diagnosing respiratory distress syndrome are known in the art and are thus not described herein in detail.

In certain embodiments, infants to be treated with the present methods require respiratory support but do not necessarily exhibit respiratory distress syndrome. These infants either have not been diagnosed with RDS or have not been treated with PS for RDS. In these infants, treatment can be initiated as soon as it is recognized that these infants require respiratory support. In certain embodiments, this will be at day 1, 2, 3, 4, 5, 6, 7, 8, 9, 10, 11, 12, 13, or 14 of life or thereabout, or between about day 3 to day 10 of the life of the infant. In certain embodiments, this can be later than day 10 of the life of the infant, e.g., day 14, day 18 or later.

PS therapy can be provided concomitantly with other forms of respiratory support. Typically, the PS therapy is initiated before the infant has been diagnosed with BPD. In certain embodiments, the present methods will prevent the infant from developing BPD.

Treatment is continued for a period of time deemed by a physician or other medical practitioner as appropriate to achieve a therapeutic or prophylactic effect. Treatment can be continued, for example, until the infant no longer requires respiratory support or even longer. Typically, treatment is continued for one to two weeks, e.g., until day 14 or day 18 of the infant's life or thereabout. However, the duration of treatment can be shorter, e.g., one week, or longer, e.g., extending three or more weeks, or until the infant is discharged from neonatal intensive care or from the hospital. For example, treatment can be continued through at least 36 weeks PMA of the infant or at least 28 days post-natal age of the infant. In certain embodiments, wherein the infant does not exhibit respiratory distress syndrome at birth but, days later, develops a condition that requires respiratory support, treatment with PS may not be initiated until well after day 3 of life of the infant and thus treatment will typically be continued past day 14 or day 18 of the infant's life. In infants born prematurely, for example, regardless of whether the infant exhibited respiratory distress syndrome at or near birth, treatment can be continued, for example, until 36 weeks PMA or even later.

In various embodiments, the PS is administered periodically or continuously throughout the treatment period, at dosages and utilizing protocols in accordance with standard and/or manufacturer's instructions (see, e.g., Example 1).

The PS selected for use in the methods of the invention can be the same as, or different from, the PS utilized for RDS. In one embodiment, the same PS is used. Any PS currently in use, or hereafter developed for use in RDS and other pulmonary conditions, is suitable for use in the present invention.

In certain aspects, a pulmonary surfactant of the present invention comprises a cationic peptide that can be derived from animal sources or synthetically. Exemplary peptides for use herein include naturally and non-naturally occurring pulmonary surfactant polypeptides, such as, for example, one or a combination of animal-derived SP-A, SP-B, SP-C, or SP-D polypeptides; recombinant SP-A, SP-B, SP-C, or SP-D polypeptides; synthetically derived SP-A, SP-B, SP-C, or SP-D polypeptides; SP-A, SP-B, SP-C, and SP-D analogs; SP-A, SP-B, SP-C, and SP-D polypeptide mimics; conservatively modified variants thereof retaining activity; and fragments thereof retaining activity. A pulmonary surfactant polypeptide mimic is generally a polypeptide that is engineered to mimic the essential attributes of human surfactant protein. In certain preferred embodiments, the pulmonary surfactant polypeptide comprises a cationic peptide that consists of at least about 10, preferably at least 11 amino acid residues, and no more than about 80, more usually fewer than about 35 and preferably fewer than about 25 amino acid residues.

Exemplary amino acid sequences of pulmonary surfactant polypeptides for use herein, methods of isolating them, and producing them by genetic engineering techniques are known in the art. See for example, U.S. Pat. Nos. 5,874,406; 5,840,527; 4,918,161; 5,827,825; 6,660,833, 5,006,343; 5,455,227; 5,223,481; 5,753,621; 5,891,844; 4,861,756; 5,272,252; 5,024,95; 5,238,920; 5,302,481; 6,022,955; 5,874,406; 5,840,527; 5,827,825; 6,013,619; 6,660,833; and International Publication Nos, WO8603408 and WO8904326, the disclosures of each of which are hereby incorporated by reference in its entirety. A preferred lung surfactant peptide for use herein is a SP-B or SP-C polypeptide, or polypeptide mimic.

A preferred synthetic pulmonary surfactant comprises one or more phospholipids and a polypeptide, in which the polypeptide, when admixed with a phospholipid, forms a synthetic pulmonary surfactant having a surfactant activity greater than the surfactant activity of the phospholipid alone. A particularly preferred pulmonary surfactant polypeptide for use herein is a SP-B polypeptide or polypeptide mimic. SP-B is the protein in natural pulmonary surfactant known to be the most important surfactant protein for surface tension lowering and promoting oxygen exchange. SP-B polypeptide mimics are small hydrophobic polypeptides, generally less than about 80 amino acids in size. Many SP-B polypeptide mimics possess a repeating hydrophobic cationic motif. Like natural SP-B polypeptide, SP-B mimics, preferably, lower surface tension of the terminal conducting airways and promote oxygen exchange.

A preferred SP-B mimetic for use in the present invention is KL4 peptide, which is a cationic peptide containing repeating lysine and leucine residues. KL4 is representative of a family of pulmonary surfactant polypeptide mimetics which are described, for example, in U.S. Pat. Nos. 5,260,273, 5,164,369, 5,407,914 and 6,613,734, each of which is hereby incorporated by reference in its entirety and for all purposes. Methods of preparing the KL4 peptide can be found in U.S. Pat. No. 5,164,369.

In certain embodiments, pulmonary surfactants polypeptide mimics refer to polypeptides with an amino acid residue sequence that has a composite hydrophobicity of less than zero, preferably less than or equal to −1, more preferably less than or equal to −2. The composite hydrophobicity value for a peptide is determined by assigning each amino acid residue in a peptide its corresponding hydrophilicity value as described in Hopp et al., *Proc. Natl. Acad. Sci.* 78: 3824-3829, 1981, which disclosure is incorporated by reference. For a given peptide, the hydrophobicity values are summed, the sum representing the composite hydrophobicity value. These hydrophobic polypeptides typically perform the function of the hydrophobic region of SP18. Accordingly, in certain embodiments, the amino acid sequence of the pulmonary surfactant polypeptide mimic mimics the pattern of hydrophobic and hydrophilic residues of SP18 and perform the function of the hydrophobic region of SP18. SP18 is a known lung surfactant apoprotein, more thoroughly described in Glasser et al., *Proc. Natl. Acad. Sci.* 84: 4007-4001, 1987, which is hereby incorporated by reference in its entirety and for all purposes. It should be understood, however, that polypeptides and other surfactant molecules of the present invention are not limited to molecules having sequences like that of native SP18. On the contrary, some preferred surfactant molecules of the present invention have little resemblance to SP18 with respect to a specific amino acid residue sequence, except that they have similar surfactant activity and alternating charged/uncharged (or hydrophobic/hydrophilic) residue sequences.

In certain embodiments, exemplary polypeptides for use herein have alternating hydrophobic and hydrophilic amino acid residue regions and are characterized as having at least 10 amino acid residues represented by the formula:

$$(Z_aU_b)_cZ_d$$

Z and U are amino acid residues such that at each occurrence Z and U are independently selected. Z is a hydrophilic amino acid residue, preferably selected from the group consisting of R, D, E and K. U is a hydrophobic amino acid residue, preferably selected from the group consisting of V, I, L, C, Y, and F. The letters, "a," "b,", "c" and "d" are numbers which indicate the number of hydrophilic or hydrophobic residues. The letter "a" has an average value of about 1 to about 5, preferably about 1 to about 3. The letter "b" has an average value of about 3 to about 20, preferably about 3 to about 12, most preferably, about 3 to about 10. The letter "c" is 1 to 10, preferably, 2 to 10, most preferably 3 to 6. The letter "d" has an average value of about 0 to 3, preferably 1 to 2.

In certain embodiments, surfactant polypeptides include a sequence having alternating groupings of amino acid residues as represented by the formula:

$$(Z_aJ_b)_cZ_d$$

wherein Z is an amino acid residue independently selected from the group consisting of R, D, E, and K; J is an α-aminoaliphatic carboxylic acid; a has an average value of about 1 to about 5; b has an average value of about 3 to about 20; c is 1 to 10; and d is 0 to 3.

In certain embodiments, polypeptides of the present invention have alternating groupings of amino acids residue regions as represented by the formula:

$$(B_aU_b)_cB_d$$

wherein B is an amino acid residue independently selected from the group consisting of H, 5-hydroxylysine, 4-hydroxyproline, and 3-hydroxyproline; and U is an amino acid residue independently selected from the group consisting of V, I, L, C, Y, and F. In one preferred variation, B is an amino acid derived from collagen and is preferably selected from the group consisting of 5-hydroxylysine, 4-hydroxyproline, and 3-hydroxyproline; a has an average value of about 1 to about 5; b has an average value of about 3 to about 20; c is 1 to 10; and d is 0 to 3.

In certain embodiments, surfactant polypeptides of the present invention include a sequence having alternating groupings of amino acid residues as represented by the formula:

$$(B_aJ_b)_cB_d$$

wherein B is an amino acid residue independently selected from the group consisting of H, 5-hydroxylysine, 4-hydroxyproline, and 3-hydroxyproline; and J is an α-aminoaliphatic carboxylic acid; a has an average value of about 1 to about 5; b has an average value of about 3 to about 20; c is 1 to 10; and d is 0 to 3.

In various embodiments including "J" in the relevant formula, J is an α-aminoaliphatic carboxylic acid having four to six carbons, inclusive. In other variations, J is an α-aminoaliphatic carboxylic acid having six or more carbons, inclusive. In yet other variations, J is selected from the group consisting of a-aminobutanoic acid, α-aminopentanoic acid, α-amino-2-methylpropanoic acid, and a-aminohexanoic acid.

In certain embodiments, surfactant polypeptides of the present invention comprise a sequence having including a sequence having alternating groupings of amino acid residues as represented by the formula:

$$(Z_aU_b)_cZ_d$$

wherein Z is an amino acid residue independently selected from the group consisting of R, D, E, and K; and U is an amino acid residue independently selected from the group consisting of V, I, L, C, Y and F; from the group consisting of V, I, L, C and F; or from the group consisting of L and C; a has an average value of about 1 to about 5; b has an average value of about 3 to about 20; c is 1 to 10; and d is 0 to 3.

In the foregoing formulas, Z and U, Z and J, B and U, and B and J are amino acid residues that, at each occurrence, are independently selected. In addition, in each of the aforementioned formulae, a generally has an average value of about 1 to about 5; b generally has an average value of about 3 to about 20; c is 1 to 10; and d is 0 to 3.

In certain embodiments, Z and B are charged amino acid residues. In other preferred embodiments, Z and B are hydrophilic or positively charged amino acid residues. In one variation, Z is preferably selected from the group consisting of R, D, E and K. In a related embodiment, Z is preferably selected from the group consisting of R and K. In yet another preferred embodiment, B is selected from the group consisting of H, 5-hydroxylysine, 4-hydroxyproline, and 3-hydroxyproline. In one preferred embodiment, B is H. In another preferred embodiment, B is a collagen constituent amino acid residue and is selected from the group consisting of 5-hydroxylysine, (δ-hydroxylysine), 4-hydroxyproline, and 3-hydroxyproline.

In certain embodiments, U and J are, preferably, uncharged amino acid residues. In another preferred embodiment, U and J are hydrophobic amino acid residues. In one embodiment, U is preferably selected from the group consisting of V, I, L, C, Y, and F. In another preferred embodiment, U is selected from the group consisting of V, I, L, C, and F. In yet another preferred embodiment, U is selected from the group consisting of L and C. In various preferred embodiments, U is L.

Similarly, in certain embodiments, B is an amino acid preferably selected from the group consisting of H, 5-hydroxylysine, 4-hydroxyproline, and 3-hydroxyproline. Alternatively, B can be selected from the group consisting of collagen-derived amino acids, which includes 5-hydroxylysine, 4-hydroxyproline, and 3-hydroxyproline.

In certain embodiments, charged and uncharged amino acids are selected from groups of modified amino acids. For example, in one preferred embodiment, a charged amino acid is selected from the group consisting of citrulline, homoarginine, or ornithine, to name a few examples. Similarly, in various preferred embodiments, the uncharged amino acid is selected from the group consisting of α-aminobutanoic acid, α-aminopentanoic acid, α-amino-2-methylpropanoic acid, and α-aminohexanoic acid.

In certain embodiments of the present invention, items "a", "b", "c" and "d" are numbers which indicate the number of charged or uncharged residues (or hydrophilic or hydrophobic residues). In various embodiments, "a" has an average value of about 1 to about 5, preferably about 1 to about 3, more preferably about 1 to about 2, and even more preferably, 1.

In various embodiments, "b" has an average value of about 3 to about 20, preferably about 3 to about 12, more preferably about 3 to about 10, even more preferably in the range of about 4-8. In one preferred embodiment, "b" is about 4.

In various embodiments, "c" is 1 to 10, preferably 2 to 10, more preferably in the range of 3-8 or 4-8, and even more preferably 3 to 6. In one preferred embodiment, "c" is about 4.

In various embodiments, "d" is 0 to 3 or 1 to 3. In one preferred embodiment, "d" is 0 to 2 or 1 to 2; in another preferred embodiment, "d" is 1.

By stating that an amino acid residue is independently selected, it is meant that at each occurrence, a residue from the specified group is selected. That is, when "a" is 2, for example, each of the hydrophilic residues represented by Z will be independently selected and thus can include RR, RD, RE, RK, DR, DD, DE, DK, and the like. By stating that "a" and "b" have average values, it is meant that although the number of residues within the repeating sequence (e.g., $Z_aU_b$) can vary somewhat within the peptide sequence, the average values of "a" and "b" would be about 1 to about 5 and about 3 to about 20, respectively.

For example, using the formula $(Z_aU_b)_cZ_d$ for the peptide designated "KL8" in Table 2 below, the formula can be rewritten as $K_1L_8K_1L_8K_1L_2$, wherein the average value of "b" is six [i.e., (8+8+2)/3=6], c is three and d is zero.

Polypeptides of the present invention can also be subject to various changes, such as insertions, deletions and substitutions, either conservative or non-conservative, where such changes provide for certain advantages in their use.

Additional residues can be added at either terminus of a polypeptide of the present invention, such as for the purpose of providing a "linker" by which such a polypeptide can be conveniently affixed to a label or solid matrix, or carrier. Labels, solid matrices and carriers that can be used with the polypeptides of this invention are known in the art.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-NH$_2$ acylation, e.g., acetylation, or thioglycolic acid amidation, terminal-carboxlyamidation, e.g., ammonia, methylamine, and the like.

In certain embodiments, exemplary SP-B polypeptide mimics that can be used in the present invention include, but are not limited to, those shown in the Table 2.

TABLE 2

Pulmonary Surfactant Mimetic Peptides

| Designation[1] | SEQ ID NO | Amino Acid Residue Sequence |
|---|---|---|
| KL4 | 1 | KLLLLKLLLLKLLLLKLLLLK |
| DL4 | 2 | DLLLLDLLLLDLLLLDLLLLD |
| RL4 | 3 | RLLLLRLLLLRLLLLRLLLLR |
| RL8 | 4 | RLLLLLLLLRLLLLLLLLRLL |
| R2L7 | 5 | RRLLLLLLLRRLLLLLLLRRL |
|  | 6 | RLLLLCLLLRLLLLLCLLLR |
|  | 7 | LLLLLCLLLRLLLLCLLLRLL |
|  | 8 | RLLLLCLLLRLLLLCLLLRLLLLCLLLR DLLLDLLLDLLLDLLLDLLLD |
| RCL1 | 9 | RLLLLCLLLRLLLLCLLLR |
| RCL2 | 10 | RLLLLCLLLRLLLLCLLLRLL |
| RCL3 | 11 | RLLLLCLLLRLLLLCLLLRLLLLCLLLR |
| KL8 | 12 | KLLLLLLLLKLLLLLLLLKLL |
| KL7 | 13 | KKLLLLLLLKKLLLLLLLKKL |

[1]The designation is an abbreviation for the indicated amino acid residue sequence.

The present invention contemplates a variety of surfactant molecules, including proteins, polypeptides, and molecules including amino acid residues, as well as a variety of surfactant compositions. A wide variety of other molecules, including uncommon but naturally occurring amino acids, metabolites and catabolites of natural amino acids, substituted amino acids, and amino acid analogs, as well as amino acids in the "D" configuration, are useful in molecules and compositions of the present invention. In addition, "designed" amino acid derivatives, analogs and mimics are also useful in various compounds, compositions and methods of the present invention, as well as polymers including backbone structures composed of non-amide linkages.

For example, in addition to the L-amino acids, amino acid metabolites such as homoarginine, citrulline, ornithine, and a-aminobutanoic acid are also useful in pulmonary surfactants. Thus, in the various formulas described above, "Charged", Z, or B can comprise homoarginine, citrulline, or ornithine, as well as a variety of other molecules as identified herein. Similarly, J can comprise α-amrinobutanoic acid (also known as α-aminobutyric acid), α-aminopentanoic acid, α-aminohexanoic acid, and a variety of other molecules identified herein.

Further, substituted amino acids which are not generally derived from proteins, but which are known in nature, are useful as disclosed herein, include the following examples: L-canavanine; 1-methyl-L-histidine; 3-methyl-L-histidine; 2-methyl L-histidine; α, ε-diaminopimelic acid (L form, meso form, or both); sarcosine; L-ornithine betaine; betaine of histidine (herzynine); L-citrulline; L-phosphoarginine; D-octopine; o-carbamyl-D-serine; γ-aminobutanoic acid; and β-lysine. D-amino acids and D-amino acid analogs, including the following, are also useful in proteins, peptides and compositions of the present invention: D-alanine, D-serine, D-valine, D-leucine, D-isoleucine, D-alloisoleucine, D-phenylalanine, D-glutamic acid, D-proline, and D-allohydroxyproline, to name some examples. The foregoing can also be used in surfactant molecules according to the present invention; particularly preferred for use accordingly are those corresponding to the formula {(Charged)$_a$(Uncharged)$_b$}$_c$(Charged)$_d$.

An extensive variety of amino acids, including metabolites and catabolites thereof, can be incorporated into molecules which display a surfactant activity. For example, molecules such as ornithine, homoarginine, citrulline, and a-aminobutanoic acid are useful components of molecules displaying surfactant activity as described herein. Surfactant molecules according to the present invention can also comprise longer straight-chain molecules; α-aminopentanoic acid and α-aminohexanoic acid are two additional examples of such useful molecules.

It should also be appreciated that the present invention encompasses a wide variety of modified amino acids, including analogs, metabolites, catabolites, and derivatives, irrespective of the time or location at which modification occurs. In essence, one can place modified amino acids into three categories: (1) catabolites and metabolites of amino acids; (2) modified amino acids generated via posttranslational modification (e.g., modification of side chains); and (3) modifications made to amino acids via non-metabolic or non-catabolic processes (e.g., the synthesis of modified amino acids or derivatives in the laboratory).

The present invention also contemplates that one can readily design side chains of the amino acids of residue units that include longer or shortened side chains by adding or subtracting methylene groups in either linear, branched chain, or hydrocarbon or heterocyclic ring arrangements. The linear and branched chain structures can also contain non-carbon atoms such as S, O, or N. Fatty acids can also be useful constituents of surfactant molecules herein. The designed side chains can terminate with (R') or without (R) charged or polar group appendages.

In addition, analogs, including molecules resulting from the use of different linkers, are also useful as disclosed herein. Molecules with side chains linked together via linkages other than the amide linkage e.g., molecules containing amino acid side chains or other side chains (R- or R'-) wherein the components are linked via carboxy- or phospho-esters, ethylene, methylene, ketone or ether linkages, to name a few examples, are also useful as disclosed herein. In essence, any amino acid side chain, R or R' group-containing molecule can be useful as disclosed herein, as long as the molecule includes alternating hydrophilic and hydrophobic residues (i.e., component molecules) and displays surfactant activity as described herein.

The present invention also contemplates molecules comprising peptide dimers joined by an appropriate linker, e.g., peptide dimers linked by cystine molecules. Such linkers or bridges can thus cross-link different polypeptide chains, dimers, trimers, and the like. Other useful linkers which can be used to connect peptide dimers and/or other peptide multimers include those listed above e.g., carboxy- or phosphoester, ethylene, methylene, ketone or ether linkages, to name a few examples.

While it is appreciated that many useful polypeptides disclosed herein comprise naturally-occurring amino acids in the "L" form which are joined via peptide linkages, it should also be understood that molecules including amino acid side chain analogs, non-amide linkages (e.g., differing backbones) can also display a significant surfactant activity and can possess other advantages, as well. For example, if it is desirable to construct a molecule (e.g., for use in a surfactant composition) that is not readily degraded, one may wish to synthesize a polypeptide molecule comprising a series of D-amino acids. Molecules comprising a series of amino acids linked via a "retro" backbone, i.e., a molecule that has internal amide bonds constructed in the reverse direction of carboxyl terminus to amino terminus, are also more difficult to degrade and can thus be useful in various applications, as described herein. For example, the following illustrates an exemplary molecule with a "retro" bond in the backbone:

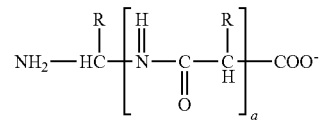

In another variation, one may wish to construct a molecule that adopts a more "rigid" conformation; one means of accomplishing this would be to add methyl or other groups to the a carbon atom of the amino acids.

As noted above, other groups besides a $CH_3$ group can be added to the a carbon atom, that is, surfactant molecules of the present invention are not limited to those incorporating a $CH_3$ at the a carbon alone. For example, any of the side chains and molecules described above can be substituted for the indicated $CH_3$ group at the a carbon component.

As used herein, the terms "analogs" and "derivatives" of polypeptides and amino acid residues are intended to encompass metabolites and catabolites of amino acids, as well as molecules which include linkages, backbones, side-chains or side-groups which differ from those ordinarily found in what are termed "naturally-occurring" L-form amino acids. (The terms "analog" and "derivative" can also conveniently be used interchangeably herein.) Thus, D-amino acids, molecules which mimic amino acids and amino acids with "designed" side chains (i.e., that can substitute for one or more amino acids in a molecule having surfactant activity) are also encompassed by the terms "analogs" and "derivatives" herein.

A wide assortment of useful surfactant molecules, including amino acids having one or more extended or substituted R or R' groups, is also contemplated by the present invention. Again, one of skill in the art should appreciate from the disclosures that one can make a variety of modifications to individual amino acids, to the linkages, and/or to the chain itself, which modifications will produce molecules falling within the scope of the present invention, as long as the resulting molecule possesses surfactant activity as described herein.

In certain methods of the present invention, a pulmonary surfactant comprises one or more lipids. In these embodiments, the surfactant composition can comprise, for example, from as little as about 0.05 to 100% weight percent lipid, so long as the resulting composition has surfactant activity. By weight percent is meant the percentage of a compound by weight in a composition by weight. Thus, a composition having 50 weight percent lipid contains, for example, 50 grams lipids per 100 grams total composition. The term "lipid" as used herein refers to a naturally occurring, synthetic or semi-synthetic (i.e., modified natural) compound which is generally amphipathic. The lipids typically comprise a hydrophilic component and a hydrophobic component. Exemplary lipids include, but are not limited, phospholipids, fatty acids, fatty alcohols, neutral fats, phosphatides, oils, glycolipids, surface-active agents (surfactants), aliphatic alcohols, waxes, terpenes and steroids. The phrase semi-synthetic (or modified natural) denotes a natural compound that has been chemically modified in some fashion. Preferably, the lipids of are fatty acids, alcohols, esters and ethers thereof, fatty amines, or combinations thereof.

Examples of phospholipids include native and/or synthetic phospholipids. Phospholipids that can be used include, but are not limited to, phosphatidylcholines, phospatidylglycerols, phosphatidylethanolamines, phosphatidylserines, phosphatidic acids, phosphatidylinositols, sphingolipids, diacylglycerides, cardiolipin, ceramides, cerebrosides and the like. Exemplary phospholipids include, but are not limited to, dipalmitoyl phosphatidylcholine (DPPC), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2), myristoyl palmitoyl phosphatidylcholine (MPPC), steroyl myristoyl phosphatidylcholine (SMPC), steroyl palmitoyl phosphatidylcholine (SPPC), palmitoyloleoyl phosphatidylcholine (POPC), palmitoyl palmitooleoyl phosphatidylcholine (PPoPC), dipalmitoyl phosphatidylethanolamine (DPPE), palmitoyloleoyl phosphatidylethanolamine (POPE), dioleoylphosphatidylethanolamine (DOPE), dimyristoyl phosphatidylethanolamine (DMPE), distearoyl phosphatidylethanolamine (DSPE), dioleoyl phosphatidylglycerol (DOPG), palmitoyloleoyl phosphatidylglycerol (POPG), dipalmitoyl phosphatidylglycerol (DPPG), dimyristoyl phosphatidylglycerol (DMPG), distearoyl phosphatidylglycerol (DSPG), dimyristoylphosphatidylserine (DMPS), distearoylphosphatidylserine (DSPS), palmitoyloleoyl phosphatidylserine (POPS), soybean lecithin, egg yolk lecithin, sphingomyelin, phosphatidylinositols, diphosphatidylglycerol, phosphatidylethanolamine, phosphatidic acids, and egg phosphatidylcholine (EPC).

Examples of fatty acids and fatty alcohols include, but are not limited to, sterols, palmitic acid, cetyl alcohol, lauric acid, myristic acid, stearic acid, phytanic acid, dipamlitic acid, and the like. Preferably, the fatty acid is palmitic acid and preferably the fatty alcohol is cetyl alcohol.

Examples of fatty acid esters include, but are not limited to, methyl palmitate, ethyl palmitate, isopropyl palmitate, cholesteryl palmitate, palmityl palmitate sodium palmitate, potassium palmitate, tripalmitin, and the like.

An example of a semi-synthetic or modified natural lipid is any one of the lipids described above which has been chemically modified. The chemical modification can include a number of modifications; however, a preferred modification is the conjugation of one or more polyethylene glycol (PEG) groups to desired portions of the lipid. Polyethylene glycol (PEG) has been widely used in biomaterials, biotechnology and medicine primarily because PEG is a biocompatible, nontoxic, nonimmunogenic and water-soluble polymer. Zhao and Harris, *ACS Symposium Series* 680: 458-72, 1997. In the area of drug delivery, PEG derivatives have been widely used in covalent attachment (i.e., "PEGylation") to proteins to reduce immunogenicity, proteolysis and kidney clearance and to enhance solubility. Zalipsky, *Adv. Drug Del. Rev.* 16: 157-82, 1995.

Lipids that have been conjugated with PEG are referred to herein as "PEG-lipids." Preferably, when PEG-lipids are used, they are present in alcohols and/or aldehydes.

The pulmonary surfactant can comprise other excipients, including, but not limited to, various sugars such as dextrose, fructose, lactose, maltose, mannitol, sucrose, sorbitol, trehalose, and the like, surfactants such as, for example, polysorbate-80, polysorbate-20, sorbitan trioleate, tyloxapol and the like, polymers such as PEG, dextran and the like, salts such as NaCl, $CaCl_2$ and the like, alcohols, such as cetyl alcohol, and buffers.

Exemplary surfactant compositions can be prepared using methods known in the art. For example, in certain embodiments, an exemplary surfactant composition comprising lipids and polypetptides can be prepared by admixing a solution of a surfactant polypeptide with a suspension of liposomes, or by admixing the surfactant polypeptide with a suspension of liposomes, or by admixing the surfactant polypeptide and phospholipids directly in the presence of organic solvent.

Preferably, the pulmonary surfactant comprises phospholipids and free fatty acids or fatty alcohols, e.g., DPPC (dipalmitoyl phosphatidylcholine), POPG (palmitoyl-oleyl phosphatidylglycerol) and palmitic acid (PA). See, for example, U.S. Pat. No. 5,789,381 the disclosure of which is incorporated herein by reference in its entirety and for all purposes.

In certain preferred embodiments, the pulmonary surfactant is lucinactant or another pulmonary surfactant formulation comprising the synthetic surfactant protein KLLLLKLLLLKLLLLKLLLLK(KL4; SEQ ID NO:1). Lucinactant, is a combination of DPPC, POPG, palmitic acid (PA) and the KL4 peptide (weight ratio of approximately 7.5:2.5:1.35:0.267). In certain embodiments, the drug product is formulated at concentrations of, for example, 10, 20, and 30 mg/ml of phospholipid content. In certain other embodiments, the drug product is formulated at greater concentrations, e.g., 40, 60, 90, 120 or more mg/ml phospholipid content, with concomitant increases in KL4 concentration.

Any pulmonary surfactant currently in use, or hereafter developed for use in respiratory distress system and other pulmonary conditions, is suitable for use in the present invention. These include naturally occurring and synthetic pulmonary surfactant. Synthetic PS, as used herein, refers to both protein-free lung surfactants and pulmonary surfactants comprising synthetic peptides, including peptide mimetics of naturally occurring surfactant protein. Current PS products include, but are not limited to, lucinactant (Surfaxin®, Discovery Laboratories, Inc., Warrington, Pa.), bovine lipid surfactant (BLES®, BLES Biochemicals, Inc. London, Ont), calfactant (Infasurt®, Forest Pharmaceuticals, St. Louis, Mo.), natural bovine surfactant (Alveofact®, Thomae, Germany), bovine surfactant (Surfactant TA®, Tokyo Tanabe, Japan), poractant alfa (Curosurf®, Chiesi Farmaceutici SpA, Parma, Italy), pumactant (Alec®, Britannia Pharmaceuticals, UK), beractant (Survanta®, Abbott Laboratories, Inc., Abbott Park, Ill.) and colfosceril palmitate (Exosurt®, GlaxoSmithKline, plc, Middlesex, U.K.). In a preferred embodiment, the PS is lucinactant or another PS formulation comprising the synthetic surfactant protein KLLLLKLLLLKLLLLKLLLLK (KL4; SEQ NO:1).

The treatment regimens described herein can be combined with other respiratory therapies. In certain embodiments, PS administration is performed on infants who are intubated and maintained on ventilation, either conventional ventilation or high frequency ventilation, for a period of time or for the entire duration of the PS treatment.

In other embodiments, alternative modes of administration can be utilized, as well as alternative PS formulations. For example, PS can be formulated for aerosolization (nebulization) and administered via nasal CPAP, nasal or naso-pharyngeal prongs in combination with low-flow oxygen, or via face mask or oxygen hood.

In certain embodiments, aerosolized pulmonary surfactant can be administered as provided in copending U.S. application Ser. No., 11/130,783, filed May 17, 2005, incorporated herein by reference in its entirety and for all purposes. Administration can be in conjunction with another noninvasive pulmonary respiratory therapy involving the administration of positive airway pressure. The term "noninvasive pulmonary respiratory therapy" refers to respiratory therapy which does not use mechanical ventilation and can include CPAP, bilevel positive airway pressure (BiPAP), synchronized intermittent mandatory ventilation (SIMV), and the like. The employment of such therapies involves the use of various respiratory gases, as would be appreciated by the skilled artisan. Respiratory gases used for noninvasive pulmonary respiratory therapy are sometimes referred to herein as "CPAP gas," "CPAP air," "nCPAP", "ventilation gas," "ventilation air," or simply "air." However, those terms are intended to include any type of gas normally used for noninvasive pulmonary respiratory therapy, including but not limited to gases and gaseous combinations listed above for use as the conditioning gas. In certain embodiments, the gas used for noninvasive pulmonary respiratory therapy is the same as the conditioning gas. In other embodiments, the respective gases are different from one another.

In certain embodiments, the pulmonary delivery methods of this invention are employed in conjunction with CPAP. It has been shown that use of CPAP allows for an increase in functional residual capacity and improved oxygenation. The larynx is dilated and supraglottic airway resistance is normal. There is also an improvement of the synchrony of respiratory thoracoabdominal movements and enhanced Hering-Breuer inflation reflex following airway occlusion. CPAP has been shown to be useful in treating various conditions such as sleep apnea, snoring, ARDS, IRDS, and the like.

In order to effect administration of CPAP, a pressure source and a delivery device or delivery apparatus are required. CPAP-producing airflow is typically generated in the vicinity of the nasal airways by converting kinetic energy from a jet of fresh humidified gas into a positive airway pressure. A continuous flow rate of breathing gas of about 5 to about 12 liters/minute generates a corresponding CPAP of about 2 to about 10 cm $H_2O$. Various modifications can be applied to the CPAP system which include sensors that can individualize the amount of pressure based on the patient's need.

Typically, flow rates and pressures suitable for achieving CPAP are based upon the characteristics of the patient being treated. Suitable flow rates and pressures can be readily calculated by the attending clinician. The present invention encompasses the use of a variety of flow rates for the ventilating gas, including low, moderate and high flow rates. Alternatively, the aerosol can be supplied without added positive pressure, i.e., without CPAP as a simultaneous respiratory therapy.

Preferably, the CPAP-generating air flow being delivered to the patient has a moisture level which will prevent unacceptable levels of drying of the lungs and airways. Thus, the CPAP-generating air is often humidified by bubbling through a hydrator, or the like to achieve a relative humidity of preferably greater that about 70%. More preferably, the humidity is greater than about 85% and still more preferably 98%.

A suitable source of CPAP-inducing airflow is the underwater tube CPAP (underwater expiratory resistance) unit. This is commonly referred to as a bubble CPAP.

Another preferred source of pressure is an expiratory flow valve that uses variable resistance valves on the expiratory limb of CPAP circuits. This is typically accomplished via a ventilator.

Another preferred source is the Infant Flow Driver or "IFD" (Electro Medical Equipment, Ltd., Brighton, Sussex, UK). IFD generates pressure at the nasal level and employs a conventional flow source and a manometer to generate a high pressure supply jet capable of producing a CPAP effect. It is suggested in the literature that the direction of the high pressure supply jet responds to pressures exerted in the nasal cavity by the patient's efforts and this reduces variations in air pressure during the inspiration cycle.

Other CPAP systems including those that contain similar features to systems just discussed are also contemplated by the present invention.

The aerosol stream generated in accordance aerosolized delivery is preferably delivered to the patient via a nasal delivery device which can involve, for example masks, single nasal prongs, binasal prongs, nasopharyngeal prongs, nasal cannulae and the like. The delivery device is chosen so as to minimize trauma, maintain a seal to avoid waste of aerosol, and minimize the work the patient must perform to breathe.

When used as an aerosol preparation, the surfactant composition can be supplied in finely divided form, optionally in combination with a suitable propellant. Useful propellants are typically gases at ambient conditions and are condensed under pressure including, for example, lower alkanes and fluorinated alkanes, such as freon. In certain embodiments wherein the surfactant composition is delivered as an aerosol, the aerosol can be packaged in a suitable container under pressure.

Suitable dosage of the surfactant, whether aerosolized or delivered as a liquid or dry powder will be dependent on the patient's age and severity of the disorder and will be readily ascertainable by the attending clinician. The actual dosage of pulmonary surfactant will of course vary according to factors such as the extent of exposure and particular status of the subject (e.g., the subject's age, size, fitness, extent of symptoms, susceptibility factors, and the like). By "effective dose" herein is meant a dose that produces effects for which it is administered.

When the surfactant is supplied to prematurely born infants as a liquid, an aliquot of the surfactant composition is delivered, preferably by intratracheal instillation, to provide an effective dose of surfactant in the lungs of the treated patient. Preferably, a single surfactant dose ranges from, for example, about 20 to about 300 mg total phospholipidid (TPL)/kg, more preferably from about 60 to about 175 mg TPL/kg. It being understood, of course, that the exact dose of surfactant will depend upon factors such as the age and condition of the patient, the severity of the condition being treated, and other factors well within the skill of the attending clinician. In certain embodiments wherein the surfactant composition is delivered as an aerosol, such as disclosed in co-pending U.S. application Ser. No. 11/130,783, filed May 17, 2005, the effective dose of lung surfactant can be, for example, from about 1 mg TPL/kg surfactant to about 1000 mg TPL/kg surfactant, preferably from about 2 mg TPL/kg surfactant to about 175 mg TPL/kg surfactant. In certain embodiments wherein the surfactant composition is delivered as a dry powder formulation, the effective dose of lung surfactant can be, for example, from about 1 mg TPL/kg surfactant to about 1000 mg or more TPL/kg surfactant, preferably from about 2 mg TPL/kg surfactant to about 175 mg TPL/kg surfactant. Other methods of delivery include lavage, lung wash, and the like. When so employed dose ranges are well within the skill of one in the art.

The frequency of dosing can vary, but typically is once every 2-3 days. In other embodiments, the patient is dosed more frequently, e.g., every 6-8 hours, twice daily, or once daily, or less frequently, e.g., twice weekly or even once weekly. In other embodiments, the patient can be dosed more frequently early in the treatment regimen, and with decreasing frequency later in the treatment regimen, e.g., once every other day for one week, followed by twice weekly until the end of the treatment period. Depending on the dosage form, e.g., aerosol or dry powder as compared with liquid instillate, the patient can be dosed continuously for part or all of the treatment period.

In other embodiments, the infant can be treated with other therapeutic, prophylactic or complementary agents, such as steroids, nitric oxide, antioxidants or reactive oxygen scavengers, bronchodilators, diuretics, antimicrobial or anti-infective agents, anti-hypertensive agents, or anti-inflammatory agents (e.g., $PLA_2$ inhibitors, protease or elastase inhibitors, PDE-4 inhibitors, to name a few), as would be appreciated by one of skill in the art. Such treatment can include concomitant administration of the PS with other therapeutic, prophylactic or complementary agents. Concomitant administration can involve concurrent (i.e. at the same time), prior, or subsequent administration of the complementary agent with respect to the administration of the pulmonary surfactant. When administered in combination, each component can be administered at the same time or sequentially in any order at different points in time. Thus, each component can be administered separately but sufficiently closely in time so as to provide the desired therapeutic effect. Concomitant administration of a PS with other therapeutic, prophylactic or complementary agents means administration of the PS and other agents at such time that both will have a therapeutic effect. A person of ordinary skill in the art, would have no difficulty determining the appropriate timing, sequence and dosages of administration for particular drugs of the present invention.

The following examples are provided to describe the invention in greater detail. Thy are intended to illustrate, not to limit, the invention.

EXEMPLARY EMBODIMENTS

Example 1

Protocol for Administration of Lucinactant to Premature Infants at Risk for Bronchopulmonary Dysplasia This example provides a protocol for administration of lucinactant to very low birthweight (VLBW) premature infants who have been intubated and received surfactants for the prevention or treatment of respiratory distress syndrome (RDS). The protocol has been used in a clinical trial to assess the safety and efficacy of lucinactant in VLBW infants at risk for developing BPD.

Two dosing regimens of lucinactant (90 mg/kg birthweight or 175 mg/kg birthweight) were utilized. Infants born with a birthweight 600 to 900 grams and who remained intubated at day of life (DOL) 3 in anticipation of worsening lung disease were treated. Treatment was administered on days 3, 5, 7, 10 and 14, if the infant remained intubated. It should be noted that Day 1 (or DOL 1) is the day on which Time 0 (time of birth) occurs and DOL 2, 3, and so on, begin at 00:00 (midnight) each subsequent day following Time 0.

Lucinactant was administered in accordance with manufacturer's instructions. Briefly, administration of lucinactant is by syringe typically attached to an end-hole catheter passed through a Bodai valve or equivalent so that that the catheter tip terminates at the distal end of the endotracheal tube. The infant is placed in a head-up left lateral decubitus position and slowly administered half the syringe volume. After allowing a brief recovery period, the infant is placed in the right lateral decubitus position and the remaining contents of the syringe are administered. The dose was administered in quarters (alternating left-right decubitus positioning) if determined to be necessary.

Efficacy of the treatment protocol was determined by making the following assessments: (1) proportion of infants remaining on mechanical ventilation or oxygen over time; (2) incidence of death or BD at 28 days and 36 weeks postmenstrual age (post-conception); (3) AUC day 3-28 fraction of inspired oxygen ($FiO_2$) and mean airway pressure; (4) pulmonary compliance as assessed by ventilator derived pressure-volume loops pre, 6 and 24 hours post dose; and (5) surrogate measures of efficacy including assessment of surface tension lowering properties of tracheal aspirates and concentration of growth factors and inflammatory mediators in tracheal aspirates collected as a part of routine neonatal intensive care.

Example 2

Protocol for Administration of Lucinactant Delivered as an Aerosol Via nCPAP for the Prevention of RDS in Premature Infants This example provides a protocol for administration of lucinactant as an aerosol via nCPA to premature infants. This protocol has been used in a pilot phase 2, open study to evaluate the feasibility, safety, and tolerability of lucinactant delivered as an aerosol via nCPAP for the prevention of RDS in premature neonates.

Lucinactant was administered using an approved vibrating machine device (Aeroneb-Pro® or equivalent) and delivered via nCPAP within 30 minutes of birth. In a first treatment group, 20 mg/ml of lucinactant was administered within the first 30 minutes of life continually over three hours. Up to three retreatments were permitted over a 48 hour period, with each treatment separated by at least 3 hours (from end of previous treatment). In a second treatment group, 20 mg/ml of lucinactant was administered within the first 30 minutes of life continually over three hours. Up to three retreatments were permitted over a 48 hour period, with each treatment separated by at least one hours (from end of previous treatment).

Qualified premature neonates were sequentially enrolled and stratified by gestational age (stratum 1:30-32 completed weeks followed by stratum 2:28-29 completed weeks) into the first treatment regimen group (3 hours on aerosol treatment/3 hours off aerosol treatment) and received aerosolized lucinactant via nCPAP. Safety and tolerability data were evaluated after enrollment of every five neonates. Once enrollment in the first treatment group was completed, neonates were sequentially enrolled and stratified into the second treatment group (3 hours on aerosol treatment/1 hours off aerosol treatment). All neonates enrolled were evaluated through 28 days of age.

All 17 neonates experienced at least 1 adverse effect regardless of relationship. A total of 83 adverse effects were reported; of these adverse effects, 8 (47.1%) were considered related to study drug, 2 (11.8%) were considered related to the device, and 6 (35.3%) were considered related to both study drug and the device. The most common adverse effects, regardless of relationship to study treatment were apnea (16/17, 94.1%), oxygen saturation decreased (12/17, 70.6%), patent ductus arteriosus (6/17, 35.3%), hypocalcemia (5/17, 29.4%). A total of 5 serious adverse effects were reported during the course of the study. Two of the serious adverse effects were considered related to the device. No deaths were occurred during this study.

The study showed that it is feasible to deliver lucinactant via nCPAP and the treatment was generally safe and well tolerated. Key observations included that 15 of the 17 neonates had no evidence of BPD at day 28.

From the foregoing description, various modifications and changes in the compositions and methods will occur to those skilled in the art. All such modifications coming within the scope of the appended claims are intended to be included therein. Each recited range includes all combinations and sub-combinations of ranges, as well as specific numerals contained therein.

All publications and patent documents cited above are hereby incorporated by reference in their entirety for all purposes to the same extent as if each were so individually denoted.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

What is claimed:

1. A method for treating an infant who has been given surfactant replacement therapy for respiratory distress syndrome and who is at risk of developing bronchopulmonary dysplasia, the method comprising: following completion of the surfactant replacement therapy for respiratory distress syndrome, administering additional pulmonary surfactant to the infant, thereby treating the infant at risk of developing the bronchopulmonary dysplasia; wherein the additional pulmonary surfactant is administered on or after day 3 of the life of the infant and is continued through at least the first week of the life of the infant.

2. The method of claim 1, wherein the administering is initiated at the next dosage interval following completion of the surfactant replacement therapy for respiratory distress syndrome.

3. The method of claim 1 wherein the administering is continued through at least day 10 of the life of the infant.

4. The method of claim 1 wherein the administering is continued through at least day 14 of the life of the infant.

5. The method of claim 1 wherein the administering is continued through at least day 18 of the life of the infant.

6. The method of claim 1 wherein the administering is initiated at day 3 of life of the infant and is continued through at least day 14 of the life of the infant.

7. A method for treating an infant who has been given surfactant replacement therapy for respiratory distress syndrome and who is at risk of developing bronchopulmonary dysplasia, the method comprising: following completion of the surfactant replacement therapy for respiratory distress syndrome administering additional pulmonary surfactant to the infant, thereby treating the infant at risk of developing the bronchopulmonary dysplasia, wherein the administering is initiated anytime from day 3 to day 14 of the life of the infant.

8. The method of claim 7 wherein the administering is initiated anytime from day 3 to day 10 of the life of the infant.

9. The method of claim 1 wherein the administering is by endotracheal administration.

10. The method of claim 1 wherein the administering is by inhalation.

11. The method of claim 1 wherein the administering is accompanied by another respiratory therapy.

12. The method of claim 11 wherein the other respiratory therapy is conventional ventilation, high frequency ventilation or continuous positive airway pressure.

13. The method of claim 11 wherein the other respiratory therapy is administration of one or more therapeutic agents.

14. The method of claim 13 wherein the other therapeutic agents are nitric oxide, steroids, antioxidants, vitamins, vitamin derivatives, reactive oxygen scavengers. bronchodilators, diuretics, antimicrobial agents, anti-infective agents, anti-hypertensive agents or anti-inflammatory agents.

15. The method of claim 1 comprising administering a synthetic pulmonary surfactant.

16. The method of claim 15 wherein the synthetic pulmonary surfactant comprises a peptide having SEQ ID NO:1.

17. A method for treating an infant requiring respiratory support and who is at risk of developing bronchopulmonary dysplasia, wherein the infant does not exhibit respiratory distress syndrome, the method comprising administering pulmonary surfactant to the infant for at least the first week of the life of the infant, thereby treating the infant at risk of developing the bronchopulmonary dysplasia.

18. The method of claim 17 wherein the administering is initiated at or after day 1 of the life of the infant and continued through at least day 28 of life of the infant.

19. The method of claim 17 wherein the administering is initiated at or after day 2 of the life of the infant.

20. The method of claim 17 wherein the administering is initiated at or after day 3 of the life of the infant.

21. The method of claim 17 wherein the administering is continued through at least day 10 of the life of the infant.

22. The method of claim 17 wherein the administering is continued through at least day 14 of the life of the infant.

23. The method of claim 17 wherein the administering is continued through at least day 18 of the life of the infant.

24. The method of claim 17 wherein the administering is initiated anytime from day 3 to one week of the life of the infant.

25. The method of claim 17 wherein the administering is by endotracheal administration.

26. The method of claim 17 wherein the administering is by inhalation.

27. The method of claim 17 wherein the administering is accompanied by another respiratory therapy.

28. The method of claim 27 wherein the other respiratory therapy is conventional ventilation, high frequency ventilation or continuous positive airway pressure.

29. The method of claim 27 wherein the other respiratory therapy is administration of one or more therapeutic agents.

30. The method of claim 29 wherein the other therapeutic agents are nitric oxide, steroids, antioxidants, vitamins, vitamin derivatives, reactive oxygen scavengers, bronchodilators, diuretics, antimicrobial agents, anti-infective agents, anti-hypertensive agents or anti-inflammatory agents.

31. The method of claim 17 comprising administering a synthetic pulmonary surfactant.

32. The method of claim 31 wherein the synthetic pulmonary surfactant comprises a peptide having SEQ ID NO:1.

33. A method for treating an infant who is at risk of developing bronchopulmonary dysplasia, wherein the infant has not been given surfactant replacement therapy, the method comprising administering pulmonary surfactant to the infant for at least the first week of the life of the infant, thereby treating the infant at risk of developing the bronchopulmonary dysplasia.

34. The method of claim 33, wherein the administering is continued through at least day 10 of the life of the infant.

35. The method of claim 33, wherein the administering is continued through at least day 14 of the life of the infant.

36. The method of claim 33, wherein the administering is continued through at least day 18 of the life of the infant.

37. The method of claim 33, wherein the administering is initiated anytime from day 3 to one week of the life of the infant.

38. The method of claim 33, wherein the administering is by endotracheal administration.

39. The method of claim 33, wherein the administering is by inhalation.

40. The method of claim 33, wherein the administering is accompanied by another respiratory therapy.

41. The method of claim 40, wherein the other respiratory therapy is conventional ventilation, high frequency ventilation or continuous positive airway pressure.

42. The method of claim 40, wherein the other respiratory therapy is administration of one or more therapeutic agents.

43. The method of claim 42, wherein the other therapeutic agents are nitric oxide, steroids, antioxidants, vitamins, vitamin derivatives, reactive oxygen scavengers, bronchodilators, diuretics, antimicrobial agents, anti-infective agents, anti-hypertensive agents or anti-inflammatory agents.

44. The method of claim 33, comprising administering a synthetic pulmonary surfactant.

45. The method of claim 44, wherein the synthetic pulmonary surfactant comprises SEQ ID NO:1.

* * * * *

SEQUENCE LISTING

```
<160> NUMBER OF SEQ ID NOS: 13

<210> SEQ ID NO 1
<211> LENGTH: 21
<212> TYPE: PRT
<213> ORGANISM: Artificial Sequence
<220> FEATURE:
<223> OTHER INFORMATION: Synthetic Construct

<400> SEQUENCE: 1

Lys Leu Leu Leu Leu Lys Leu Leu Leu Leu Lys Leu Leu Leu Leu Lys
1               5                   10                  15

Leu Leu Leu Leu Lys
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic Construct

<400> SEQUENCE: 2

Asp Leu Leu Leu Leu Asp Leu Leu Leu Leu Asp Leu Leu Leu Leu Asp
1               5                   10                  15

Leu Leu Leu Leu Asp
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct

<400> SEQUENCE: 3

Arg Leu Leu Leu Leu Arg Leu Leu Leu Leu Arg Leu Leu Leu Leu Arg
1               5                   10                  15

Leu Leu Leu Leu Arg
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic Construct

<400> SEQUENCE: 4

Arg Leu Leu Leu Leu Leu Leu Leu Leu Arg Leu Leu Leu Leu Leu Leu
1               5                   10                  15
```

Leu Leu Arg Leu Leu
         20

<210> SEQ ID NO 5
<211> LENGTH: 21
<212> TYPE: PRT
<213> ORGANISM: Artificial Sequence
<220> FEATURE:
<223> OTHER INFORMATION: Synthetic Construct

<400> SEQUENCE: 5

Arg Arg Leu Leu Leu Leu Leu Leu Arg Arg Leu Leu Leu Leu Leu
1               5                   10                  15

Leu Leu Arg Arg Leu
         20

<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

Arg Leu Leu Leu Cys Leu Leu Leu Arg Leu Leu Leu Leu Cys
1               5                   10                  15

Leu Leu Leu Arg
         20

<210> SEQ ID NO 7
<211> LENGTH: 21
<212> TYPE: PRT
<213> ORGANISM: Artificial Sequence
<220> FEATURE:
<223> OTHER INFORMATION: Synthetic Construct

<400> SEQUENCE: 7

Leu Leu Leu Leu Leu Cys Leu Leu Arg Leu Leu Leu Leu Cys Leu
1               5                   10                  15

Leu Leu Arg Leu Leu
         20

<210> SEQ ID NO 8
<211> LENGTH: 49
<212> TYPE: PRT
<213> ORGANISM: Artificial Sequence
<220> FEATURE:
<223> OTHER INFORMATION: Synthetic Construct

<400> SEQUENCE: 8

Arg Leu Leu Leu Leu Cys Leu Leu Arg Leu Leu Leu Leu Cys Leu
1               5                   10                  15

Leu Leu Arg Leu Leu Leu Cys Leu Leu Arg Asp Leu Leu Leu
             20                  25                  30

Asp Leu Leu Leu Asp Leu Leu Leu Asp Leu Leu Leu Asp Leu Leu Leu
             35                  40                  45

Asp

<210> SEQ ID NO 9
<211> LENGTH: 19
<212> TYPE: PRT
<213> ORGANISM: Artificial Sequence
<220> FEATURE:

```
<223> OTHER INFORMATION: Synthetic Construct

<400> SEQUENCE: 9

Arg Leu Leu Leu Leu Cys Leu Leu Arg Leu Leu Leu Leu Cys Leu
1               5                   10                  15

Leu Leu Arg

<210> SEQ ID NO 10
<211> LENGTH: 21
<212> TYPE: PRT
<213> ORGANISM: Artificial Sequence
<220> FEATURE:
<223> OTHER INFORMATION: Synthetic Construct

<400> SEQUENCE: 10

Arg Leu Leu Leu Leu Cys Leu Leu Leu Arg Leu Leu Leu Leu Cys Leu
1               5                   10                  15

Leu Leu Arg Leu Leu
            20

<210> SEQ ID NO 11
<211> LENGTH: 28
<212> TYPE: PRT
<213> ORGANISM: Artificial Sequence
<220> FEATURE:
<223> OTHER INFORMATION: Synthetic Construct

<400> SEQUENCE: 11

Arg Leu Leu Leu Leu Cys Leu Leu Leu Arg Leu Leu Leu Leu Cys Leu
1               5                   10                  15

Leu Leu Arg Leu Leu Leu Leu Cys Leu Leu Leu Arg
            20                  25

<210> SEQ ID NO 12
<211> LENGTH: 21
<212> TYPE: PRT
<213> ORGANISM: Artificial Sequence
<220> FEATURE:
<223> OTHER INFORMATION: Synthetic Construct

<400> SEQUENCE: 12

Lys Leu Leu Leu Leu Leu Leu Leu Leu Lys Leu Leu Leu Leu Leu Leu
1               5                   10                  15

Leu Leu Lys Leu Leu
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic Construct

<400> SEQUENCE: 13

Lys Lys Leu Leu Leu Leu Leu Leu Leu Lys Lys Leu Leu Leu Leu Leu
1               5                   10                  15

Leu Leu Lys Lys Leu
            20
```